(12) United States Patent
Keltner et al.

(10) Patent No.: US 10,307,610 B2
(45) Date of Patent: *Jun. 4, 2019

(54) METHOD AND APPARATUS FOR LIGHT-ACTIVATED DRUG THERAPY

(71) Applicant: LIGHT SCIENCES ONCOLOGY, INC., Bellevue, King County, WA (US)

(72) Inventors: Llew Keltner, Portland, OR (US); Jay Winship, Bellevue, WA (US); Erik Hagstrom, Woodinville, WA (US); Frank Zheng, Kirkland, WA (US); James C. Chen, Clyde Hill, WA (US); Joseph M. Hobbs, Issaquah, WA (US)

(73) Assignee: LIGHT SCIENCES ONCOLOGY INC., Bellevue, King County, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/406,057

(22) Filed: Jan. 13, 2017

(65) Prior Publication Data

US 2017/0128741 A1    May 11, 2017

Related U.S. Application Data (63) Continuation-in-part of application No. 15/091,270, filed on Apr. 5, 2016, which is a continuation-in-part (Continued)

(30) Foreign Application Priority Data

Jan. 18, 2006    (CN) .................... 2006 2 0088987 U (51) Int. Cl.
*A61N 5/06* (2006.01)
*A61K 41/00* (2006.01)
(Continued)

(52) U.S. Cl.
CPC .......... *A61N 5/062* (2013.01); *A61K 41/0071* (2013.01); *A61N 5/0601* (2013.01);
(Continued)

(58) Field of Classification Search
CPC .. A61B 2018/00547; A61B 2018/2261; A61K 41/0071; A61N 5/062;
(Continued)

(56) References Cited

U.S. PATENT DOCUMENTS

| 4,128,173 A | 12/1978 | Lazarus et al. |
|---|---|---|
| 4,408,263 A | 10/1983 | Sternlicht |

(Continued)

FOREIGN PATENT DOCUMENTS

| CN | 1154444 A | 7/1997 |
|---|---|---|
| CN | 2607149 Y | 3/2004 |

(Continued)

OTHER PUBLICATIONS

European Patent Office, Extended European Search Report, issued in EP Patent Application 07718240.0, dated Jun. 3, 2015, 6 pages.

(Continued)

*Primary Examiner* — Aaron F Roane
(74) *Attorney, Agent, or Firm* — Troutman Sanders LLP (57) ABSTRACT

A prostate treatment system having a light delivery device positionable in a transurethral device for treatment of benign prostatic hyperplasia (BPH). The light delivery device includes light generator, such as light emitting diodes (LED), laser diodes (LDs) or a diffusion quartz fiber tip connected to a light generator or a light emitting polymer which produces light at a selected wavelength or waveband or alternative sources of suitable light energy. The treatment device may further include a temperature monitoring system for monitoring the temperature at the treatment site. A light-activated drug is administered to the treatment site (Continued)

prior to light activation. The light-activated drug therapy induces cell death of the target tissue. The device provides a minimally invasive transurethral method for treatment of BPH or prostate cancer.

20 Claims, 4 Drawing Sheets

Related U.S. Application Data of application No. 12/161,323, filed as application No. PCT/US2007/001324 on Jan. 18, 2007, now abandoned.

(51) Int. Cl.
| | | |
|---|---|---|
| A61B 17/00 | (2006.01) | |
| A61B 17/22 | (2006.01) | |
| A61B 18/00 | (2006.01) | |
| A61B 18/22 | (2006.01) | |
| A61N 5/067 | (2006.01) | |

(52) U.S. Cl.
CPC .. *A61N 5/0603* (2013.01); *A61B 2017/00084* (2013.01); *A61B 2017/00274* (2013.01); *A61B 2017/22068* (2013.01); *A61B 2018/00285* (2013.01); *A61B 2018/00547* (2013.01); *A61B 2018/00821* (2013.01); *A61B 2018/2261* (2013.01); *A61N 2005/061* (2013.01); *A61N 2005/0602* (2013.01); *A61N 2005/063* (2013.01); *A61N 2005/067* (2013.01); *A61N 2005/0652* (2013.01)

(58) Field of Classification Search
CPC ............... A61N 5/0601; A61N 5/0603; A61N 2005/0602; A61N 2005/061; A61N 2005/063; A61N 2005/0652; A61N 2005/067
USPC ......................................................... 607/88
See application file for complete search history.

(56) References Cited

U.S. PATENT DOCUMENTS

| | | | |
|---|---|---|---|
| 4,423,725 A | 1/1984 | Baran et al. | |
| 4,445,892 A | 5/1984 | Hussein et al. | |
| 4,470,407 A | 9/1984 | Hussein | |
| 4,522,302 A | 6/1985 | Paikoff | |
| 4,538,622 A | 9/1985 | Samson et al. | |
| 4,545,390 A | 10/1985 | Leary | |
| 4,656,186 A | 4/1987 | Bommer et al. | |
| 4,675,338 A | 6/1987 | Bommer et al. | |
| 4,693,885 A | 9/1987 | Bommer et al. | |
| 4,763,654 A | 8/1988 | Jang | |
| 4,773,899 A | 9/1988 | Spears | |
| 4,799,479 A | 1/1989 | Spears | |
| 4,820,349 A | 4/1989 | Saab | |
| 4,906,241 A | 3/1990 | Noddin et al. | |
| 4,961,738 A | 10/1990 | Mackin | |
| 4,977,177 A | 12/1990 | Bommer et al. | |
| 4,983,167 A | 1/1991 | Sahota | |
| 4,997,639 A | 3/1991 | Aizawa et al. | |
| 5,004,811 A | 4/1991 | Bommer et al. | |
| 5,019,042 A | 5/1991 | Sahota | |
| 5,019,075 A | 5/1991 | Spears et al. | |
| 5,026,366 A | 6/1991 | Leckrone | |
| 5,034,001 A | 7/1991 | Garrison et al. | |
| 5,066,274 A | 11/1991 | Bommer et al. | |
| 5,071,407 A | 12/1991 | Termin et al. | |
| 5,090,958 A | 2/1992 | Sahota | |
| 5,104,392 A | 4/1992 | Kittrell et al. | |
| 5,129,889 A | 7/1992 | Hahn et al. | |
| 5,147,377 A | 9/1992 | Sahota | |
| 5,160,321 A | 11/1992 | Sahota | |
| 5,169,395 A | 12/1992 | Narciso, Jr. | |
| 5,176,619 A | 1/1993 | Segalowitz | |
| 5,178,616 A | 1/1993 | Uemiya et al. | |
| 5,217,456 A | 6/1993 | Narciso, Jr. | |
| 5,226,430 A | 7/1993 | Spears et al. | |
| 5,246,447 A * | 9/1993 | Rosen ............... | A61B 17/22022 601/24 |
| 5,267,959 A | 12/1993 | Forman | |
| 5,290,275 A | 3/1994 | Kittrell et al. | |
| 5,304,214 A | 4/1994 | DeFord et al. | |
| 5,308,861 A | 5/1994 | Aizawa et al. | |
| 5,330,465 A | 7/1994 | Doiron et al. | |
| 5,358,485 A | 10/1994 | Vance et al. | |
| 5,370,608 A | 12/1994 | Sahota et al. | |
| 5,370,675 A | 12/1994 | Edwards et al. | |
| 5,383,467 A | 1/1995 | Auer et al. | |
| 5,406,960 A | 4/1995 | Corso, Jr. | |
| 5,409,483 A | 4/1995 | Campbell et al. | |
| 5,415,654 A | 5/1995 | Daikuzono | |
| 5,417,653 A | 5/1995 | Sahota et al. | |
| 5,430,051 A | 7/1995 | Aizawa et al. | |
| 5,441,497 A | 8/1995 | Narciso, Jr. | |
| 5,445,608 A | 8/1995 | Chen et al. | |
| 5,454,794 A | 10/1995 | Narciso, Jr. et al. | |
| 5,456,661 A | 10/1995 | Narciso, Jr. | |
| 5,567,409 A | 10/1996 | Aizawa et al. | |
| 5,582,171 A | 12/1996 | Chornenky et al. | |
| 5,607,419 A | 3/1997 | Amplatz et al. | |
| 5,609,591 A | 3/1997 | Daikuzono | |
| 5,633,275 A | 5/1997 | Mori et al. | |
| 5,634,921 A | 6/1997 | Hood et al. | |
| 5,643,334 A | 7/1997 | Eckhouse et al. | |
| 5,662,712 A | 9/1997 | Pathak et al. | |
| 5,698,866 A | 12/1997 | Doiron et al. | |
| 5,700,243 A | 12/1997 | Narciso, Jr. | |
| 5,766,234 A | 6/1998 | Chen et al. | |
| 5,766,237 A | 6/1998 | Cragg | |
| 5,766,558 A | 6/1998 | Letzsch et al. | |
| 5,775,331 A | 7/1998 | Raymond et al. | |
| 5,779,697 A | 7/1998 | Glowa et al. | |
| 5,779,731 A | 7/1998 | Leavitt | |
| 5,782,896 A | 7/1998 | Chen et al. | |
| 5,800,478 A | 9/1998 | Chen et al. | |
| 5,814,008 A | 9/1998 | Chen et al. | |
| 5,827,186 A | 10/1998 | Chen et al. | |
| 5,830,210 A | 11/1998 | Rudko et al. | |
| 5,851,221 A | 12/1998 | Rieder et al. | |
| 5,861,020 A | 1/1999 | Schwarzmaier | |
| 5,865,840 A | 2/1999 | Chen | |
| 5,876,426 A | 3/1999 | Kume et al. | |
| 5,876,427 A | 3/1999 | Chen et al. | |
| 5,947,958 A | 9/1999 | Woodard et al. | |
| 5,951,543 A | 9/1999 | Brauer | |
| 5,976,106 A | 11/1999 | Verin et al. | |
| 5,997,569 A | 12/1999 | Chen et al. | |
| 5,997,571 A | 12/1999 | Farr et al. | |
| 6,013,053 A | 1/2000 | Bower et al. | |
| 6,024,740 A | 2/2000 | Lesh et al. | |
| 6,058,323 A | 5/2000 | Lemelson | |
| 6,086,558 A | 7/2000 | Bower et al. | |
| 6,096,066 A | 8/2000 | Chen et al. | |
| 6,128,524 A | 10/2000 | Yoneya et al. | |
| 6,146,409 A | 11/2000 | Overholt et al. | |
| 6,159,236 A | 12/2000 | Biel | |
| 6,162,214 A | 12/2000 | Mueller et al. | |
| 6,171,299 B1 | 1/2001 | Bonutti | |
| 6,175,669 B1 | 1/2001 | Colston et al. | |
| 6,193,676 B1 | 2/2001 | Winston et al. | |
| 6,203,537 B1 * | 3/2001 | Adrian ................ | A61B 18/26 601/4 |
| 6,210,425 B1 | 4/2001 | Chen | |
| RE37,180 E | 5/2001 | Mori et al. | |
| 6,231,568 B1 | 5/2001 | Loeb et al. | |
| 6,238,426 B1 | 5/2001 | Chen | |
| 6,240,925 B1 | 6/2001 | McMillan et al. | |
| 6,245,012 B1 | 6/2001 | Kleshinski | |
| 6,254,571 B1 | 7/2001 | Hart | |

(56) References Cited

U.S. PATENT DOCUMENTS

| | | |
|---|---|---|
| 6,254,599 B1 | 7/2001 | Lesh et al. |
| 6,273,904 B1 | 8/2001 | Chen et al. |
| 6,290,668 B1 | 9/2001 | Gregory et al. |
| 6,299,599 B1 | 10/2001 | Pham et al. |
| 6,319,273 B1 | 11/2001 | Chen et al. |
| 6,336,934 B1 | 1/2002 | Gilson et al. |
| 6,344,050 B1 | 2/2002 | Chen |
| 6,350,772 B1 | 2/2002 | Kuroiwa et al. |
| 6,355,030 B1 | 3/2002 | Aldrich et al. |
| 6,413,495 B1 | 7/2002 | Aizawa et al. |
| 6,416,511 B1 | 7/2002 | Lesh et al. |
| 6,416,531 B2 | 7/2002 | Chen |
| 6,443,978 B1 | 9/2002 | Zharov |
| 6,445,011 B1 | 9/2002 | Hirano et al. |
| 6,454,789 B1 | 9/2002 | Chen et al. |
| 6,468,244 B1 | 10/2002 | Leone et al. |
| 6,485,502 B2 | 11/2002 | Don Michael et al. |
| 6,496,737 B2 | 12/2002 | Rudie et al. |
| 6,508,784 B1 | 1/2003 | Shu |
| 6,540,767 B1 | 4/2003 | Walak et al. |
| 6,562,031 B2 | 5/2003 | Chandrasekaran et al. |
| 6,562,058 B2 | 5/2003 | Seguin et al. |
| 6,575,965 B1 | 6/2003 | Fitch et al. |
| 6,575,966 B2 | 6/2003 | Lane et al. |
| 6,585,655 B2 | 7/2003 | Crowley |
| 6,602,274 B1 | 8/2003 | Chen |
| 6,605,030 B2 | 8/2003 | Weinberger |
| 6,616,629 B1 | 9/2003 | Verin et al. |
| 6,634,765 B2 | 10/2003 | Lin |
| 6,653,337 B2 | 11/2003 | Kuroiwa et al. |
| 6,656,174 B1 | 12/2003 | Hegde et al. |
| 6,661,167 B2 | 12/2003 | Eliashevich et al. |
| 6,689,380 B1 | 2/2004 | Marchitto et al. |
| 6,749,623 B1 | 6/2004 | Hsi et al. |
| 6,784,460 B2 | 8/2004 | Ng et al. |
| 6,811,562 B1 | 11/2004 | Pless |
| 6,830,584 B1 | 12/2004 | Seguin |
| 6,872,205 B2 | 3/2005 | Lesh et al. |
| 6,899,723 B2 | 5/2005 | Chen |
| 6,953,457 B2 | 10/2005 | Farr et al. |
| 6,958,498 B1 | 10/2005 | Shelton et al. |
| 6,962,584 B1 | 11/2005 | Stone et al. |
| 6,984,655 B1 | 1/2006 | Mori et al. |
| 6,986,782 B2 | 1/2006 | Chen et al. |
| 7,015,240 B2 | 3/2006 | North et al. |
| 7,018,395 B2 | 3/2006 | Chen |
| 7,048,756 B2 | 5/2006 | Eggers et al. |
| RE39,357 E | 10/2006 | Yoneya et al. |
| 7,252,677 B2 | 8/2007 | Burwell et al. |
| 7,396,354 B2 | 7/2008 | Rychnovsky et al. |
| 7,405,208 B2 | 7/2008 | Santi et al. |
| 7,498,029 B2 | 3/2009 | Hasan et al. |
| 7,667,039 B2 | 2/2010 | Garcia-Echeverria et al. |
| 7,730,894 B2 | 6/2010 | Burwell et al. |
| 7,943,562 B2 | 5/2011 | Lee et al. |
| 7,993,640 B2 | 8/2011 | Chen |
| 2001/0029337 A1 | 10/2001 | Pantages et al. |
| 2001/0049502 A1 | 12/2001 | Chen |
| 2002/0004053 A1 | 1/2002 | Biel |
| 2002/0127224 A1 | 9/2002 | Chen |
| 2002/0127230 A1 | 9/2002 | Chen |
| 2002/0193850 A1 | 12/2002 | Selman |
| 2003/0018371 A1 | 1/2003 | Chen |
| 2003/0065315 A1 | 4/2003 | Hareyama et al. |
| 2003/0109813 A1 | 6/2003 | Chen |
| 2003/0114434 A1 | 6/2003 | Chen et al. |
| 2003/0114744 A1 | 6/2003 | Pantages et al. |
| 2003/0130649 A1* | 7/2003 | Murray ............... A61B 18/22 606/3 |
| 2003/0167033 A1 | 9/2003 | Chen et al. |
| 2003/0195495 A1 | 10/2003 | Ryan et al. |
| 2003/0208249 A1 | 11/2003 | Chen |
| 2004/0093044 A1 | 5/2004 | Rychnovsky et al. |
| 2004/0122419 A1 | 6/2004 | Neuberger |
| 2005/0004510 A1 | 1/2005 | Chen |
| 2005/0013812 A1 | 1/2005 | Dow et al. |
| 2005/0038419 A9 | 2/2005 | Arnold et al. |
| 2005/0075704 A1 | 4/2005 | Tu et al. |
| 2005/0085455 A1 | 4/2005 | Chen |
| 2005/0106710 A1* | 5/2005 | Friedman ........... A61M 25/1011 435/287.1 |
| 2005/0113815 A1 | 5/2005 | Ritchie et al. |
| 2005/0125002 A1* | 6/2005 | Baran ............... A61M 25/0041 606/108 |
| 2005/0131510 A1 | 6/2005 | Chen et al. |
| 2005/0187597 A1 | 8/2005 | Vanderschuit |
| 2005/0196401 A1 | 9/2005 | Chen |
| 2005/0197534 A1 | 9/2005 | Barbato et al. |
| 2005/0228260 A1 | 10/2005 | Burwell et al. |
| 2005/0251131 A1 | 11/2005 | Lesh |
| 2005/0279354 A1 | 12/2005 | Deutsch et al. |
| 2006/0067889 A1 | 3/2006 | Pallenberg et al. |
| 2006/0211639 A1 | 9/2006 | Bratzler et al. |
| 2006/0265031 A1 | 11/2006 | Skwarek et al. |
| 2006/0282132 A1 | 12/2006 | Arai et al. |
| 2007/0002582 A1 | 1/2007 | Burwell et al. |
| 2007/0010782 A1 | 1/2007 | Doty et al. |
| 2007/0038204 A1 | 2/2007 | Chen et al. |
| 2007/0059316 A1 | 3/2007 | Pallenberg et al. |
| 2007/0129776 A1 | 6/2007 | Robins et al. |
| 2007/0142880 A1 | 6/2007 | Barnard et al. |
| 2007/0260295 A1 | 11/2007 | Chen et al. |
| 2008/0021210 A1 | 1/2008 | Xu et al. |
| 2008/0269846 A1 | 10/2008 | Burwell et al. |
| 2010/0274330 A1 | 10/2010 | Burwell et al. |
| 2011/0008372 A1 | 1/2011 | Chen |
| 2011/0236402 A1 | 9/2011 | Chen |

FOREIGN PATENT DOCUMENTS

| | | |
|---|---|---|
| EP | 0 297 190 A1 | 1/1989 |
| EP | 0 755 697 A2 | 1/1997 |
| EP | 0 820 786 A2 | 1/1998 |
| EP | 1610865 A2 | 1/2006 |
| JP | H02-185269 A | 7/1990 |
| JP | 03094780 U | 4/1991 |
| JP | H07-095986 | 4/1995 |
| JP | 09502904 | 3/1997 |
| JP | 9000649 | 7/1997 |
| JP | 2000515779 A | 11/2000 |
| JP | 2001505100 A | 4/2001 |
| JP | 2001-129094 A | 5/2001 |
| JP | 2001509050 A | 7/2001 |
| JP | 2001517507 A | 10/2001 |
| JP | 2002534235 A | 10/2002 |
| WO | 9304727 A1 | 3/1993 |
| WO | 1995008949 A1 | 4/1995 |
| WO | 96/00527 A2 | 1/1996 |
| WO | 96/29943 A1 | 10/1996 |
| WO | 97/32520 A1 | 9/1997 |
| WO | 9803224 A1 | 1/1998 |
| WO | 9822184 A1 | 5/1998 |
| WO | 98/32493 A1 | 7/1998 |
| WO | 9832492 A1 | 7/1998 |
| WO | 9915236 A1 | 4/1999 |
| WO | 0041768 A1 | 7/2000 |
| WO | 01/89598 A2 | 11/2001 |
| WO | 2002024199 A1 | 3/2002 |
| WO | 2003074566 A2 | 9/2003 |
| WO | 2004062728 A1 | 7/2004 |
| WO | 04/82736 A2 | 9/2004 |
| WO | 2004105597 A1 | 12/2004 |
| WO | 2004112902 A1 | 12/2004 |
| WO | 2005004704 A2 | 1/2005 |
| WO | 2005077457 A1 | 8/2005 |
| WO | 2006036968 A2 | 4/2006 |
| WO | 2007084608 A2 | 7/2007 |

OTHER PUBLICATIONS

Schmid et al., "A phase IIII study of bortezomib and capecitabine in patients with metastatic breast cancer previously treated with (56) References Cited

OTHER PUBLICATIONS taxanes and/or anthracyclines," Annals of Oncology, vol. 19: 871-876, 2008.

Schumacher et al., "Immunosensitization of Tumor Cells to Dendritic Cell Activated Immune Responses with the Proteasome Inhibitor Bortezomib (PS-341, Velcade)," The Journal of Immunology, vol. 176: 4757-4765, 2006.

Waldmann, Thomas, "Effective Cancer Therapy Through Immunomodulation," Annu. Rev. Med., vol. 57: 65-81, 2006.

Wang et al., "A phase 1111 safety and efficacy study of intra tumoral light-activated drug therapy using talaporfin sodium in patients with inoperable hepatocellular carcinoma," ANSO Annual Meeting Abstracts: 2pp, 2009.

Wang, Rong-fu., "Regulatory T Cells in Tumor Immunity: Role of Toll-Like Receptors," Cancer Immunotherapy, Chapter 15: 277-287, 2007.

Whiteside, Theresa, "The Role of Immune Cells in the Tumor Microenvironment," Cancer Treatment and Research, vol. 130, Chapter 5: 103-124, 2006.

Widen et al., "Overcoming immunosuppressive mechanisms," Annals of Oncology, vol. 19, Supplement 7: vii241-vii247, 2008.

Wojtowicz-Praga, Slawomir., "Reversal of Tumor-Induced Immunosuppression: A New Approach to Cancer Therapy," Journal of Immunotherap , vol. 20, No. 3: 165-177, 1997.

Yakirevich et al., "Regulatory T Lymphocytes: Pivotal Components of the Host Antitumor Response," Journal of Clinical Oncology, vol. 25, No. 18: 2506-2508, 2007.

Yang et al., "Bortezomib (VEL CAD E) in metastatic breast cancer: pharmacodynamics, biological effects, and prediction of clinical benefits," Annals of Oncology, vol. 17: 813-817, 2006.

Yu et al., "Priming of naïve T cells inside tumors leads to eradication of established tumors," Nature Immunology, vol. 5, No. 2: 141-149, 2004.

Zhang et al., "Generation of effective vaccines against liver cancer by using photodynamic therapy," Lasers Med Sci: 4pp., 2008.

Zwierzina, H., "Combining immunotherapy with classical anticancer therapy," Annals of Oncology, vol. 19, Supplement 7: vii252-vii255, 2008.

Unknown, "A Phase 3 Study of Talaporfin Sodium and Interstitial Light Emitting Diodes Treating Hepatocellular Carcinoma (HCC)," Study NCT00355355. 4pp., 2009.

Unknown, "Phase 3 Trial of LitxTM Plus Chemotherapy vs. Chemotherapy Only Treating Colorectal Cancer Patients With Recurrent Liver Metastatases," Study NCT00440310. 4pp., 2009.

Decker, Christine. "OSHU Cancer Institute Finds That Drug Stimulated Immune System in Prostate Cancer." Medical News Today, Jun. 4, 2008, 3 pp. <http://www. medicalnewstoday.com/articles/109743.php>.

Wolchok et al. "The Mechanism of Anti-CTLA-4 Activity and the Negative Regulation of T-Cell Activation." The Oncologist, vol. 13, Oct. 2008, 9 pp. http://theoncoloistalhamedressor/ci/content/full/13/sue4/2.

Ferrario et al. "Survivin, a Member of the Inhibitor of Apoptosis Family, Is Induced by Photodynamic Therapy and Is a Target for Improving Treatment Response." Cancer Research. May 15, 2007; 67 (10): 4989-95.

Sydor et al. "Development of 17-allylamino-17-demethoxygeldanamycin hydroquinone hydrochloride (IPI-504), an anti-cancer agent directed against Hsp90." Proc. Natl. Acad. Sci. USA. Nov. 14, 2006; 103 (46): 17408-13.

Blank et al. "Enhanced Ubiquitinylation of Heat Shock Protein 90 as a Potential Mechanism for Mitotic Cell Death in Cancer Cells Induced with Hypericin." Cancer Research. Dec. 1, 2003; 63 (23): 8241-7.

Schneider-Yin et al. "Hypericin and 5-aminolevulinic acid-induced protoporphyrin IX induce enhanced phototoxicity in human endometrial cancer cells with non-coherent white light." Photodiagnosis Photodynamic Therapy. Mar. 2009; 6(1): 12-18.

Lilge et al. "Apoptosis induced in vivo by photodynamic therapy in normal brain and intracranial tumour tissue." British Journal of Cancer. Oct. 2000; 83 (8): 1110-7.

Ortel et al. "Differentiation enhances aminolevulinic acid-dependent photodynamic treatment of LNCaP prostate cancer cells." British Journal of Cancer. Nov. 18, 2002; 87 (11): 1321-7.

Comer et al. "Photodynamic Therapy: Combined Modality Approaches Targeting the Tumor Microenvironment." Lasers in Surgery and Medicine. Jun. 2006; 38 (5): 516-21.

Song et al. "Antitumor activity and molecular effects of the novel heat shock protein 90 inhibitor, IPI-504, in pancreatic cancer." Molecular Cancer Therapeutics. Oct. 2008; 7 (10): 3275-84.

Patterson et al. "IPI-SO4, a novel and soluble HSP-90 inhibitor, blocks the unfolded protein response in multiple myeloma cells." Cancer Chemother. Pharmacol. May 2008; 61 (6): 923-32.

Abramson et al. "The heat shock protein 90 inhibitor IPI-SO4 induces apoptosis of AKT-dependent diffuse large 8-cell lymphomas." Br. J. Haematology. Feb. 2009; 144 (3): 358-66.

Ferrario et al. "Targeting the 90 kDa Heat Shock Protein Improves Photodynamic Therapy." Cancer Lett. Mar. 2010; 289: 188-94.

Krammer et al. "Molecular Response to Hypericin-Induced Photodamage." Current Medicinal Chemistry. 2012; 19 (6): 793-8.

Nagae, T.; Aizawa, K.; Uchimura, N.' Tani, D.; Abe, M.; Fujishima, K.; Wilson, S.; and Ishimaru, S. "Endovascular Photodynamic Therapy Using Mono-L-Aspartyl-Chlorin e6 to Inhibit Intimal Hyperplasia in Balloon-Injured Rabbit Arteries," Lasers in Surgery and Medicine, 28:381-388 (2001). © 2001 Wiley-Liss, Inc.

Nordenstrom, Bjorn. "New Instruments for Catheterization and Angiocardiography," Department of Roentgenology, Thoraxkliniken, Karolinska Sjukhuset, Stockholm, Sweden. Aug. 1965. pp. 256-259.

Weber, Jeffrey., "Review: Anti-CTLA-4 Antibody Ipilmumab: Case Studies of Clinical Response and Immune-Related Adverse Events." The Oncologist, vol. 12: 864-872, 2007.

N.a., "Photodynamic Therapy for Cancer Fact Sheet." National Cancer Institute: pp. 1-3, 2004.

Chen et al., "New Technology for Deep Light Distribution in Tissue for Phototherapy", The Cancer Journal, Mar./Apr. 2002, vol. 8, Issue 2, p. 154-163.

Japan Patent Office, Office Action, counterpart Japanese Patent Application 2008-551389, dated Sep. 10, 2012, 5 pages (including English Translation).

Cowles, R.S. III et al. "A Prospective Randomized Comparison of Transurethral Resection to Visual Laser Ablation of the Prostate for the Treatment of Benign Prostatic Hyperplasia," Urology, vol. 46, No. 2, 1995, pp. 155-160.

Gomez-Sancha, F. "BPH in the next millennium: a glimpse to the future," Prostate Cancer and Prostatic Diseases, 2 Suppl 4, 1999, pp. S21-S25.

Francisca, E.A.E. et al. "Tolerability of 3.5 versus 2.5 High-Energy Transurethral Microwave Thermotherapy," European Urology, vol. 38, 2000, pp. 59-63.

Holtgrewe, H. L. "Socioeconomics and Trends in the Management of Benign Prostatic Hyperplasia: United States Perspective," Chapter 3 in Benign Prostatic Hyperplasia, by P. Narayan. Churchill Livingston, 2000, pp. 53-60.

Kupeli, S. et al. "Randomized Study of Transurethral Resection of the Prostate and Combined Transurethral Resection and Vaporization of the Prostate as a Therapeutic Alternative in Men with Benign Prostatic Hyperplasia," Journal of Endourology, vol. 15, No. 3, Apr. 2001, pp. 317-321.

Schelin, S. "Mediating Transurethral Microwave Thermotherapy by Intraprostatic and Periprostatic Injections of Mepivacaine Epinephrine: Effects on Treatment Time, Energy Consumption, and Patient Comfort," Journal of Endourology, vol. 16, No. 2, Mar. 2002, pp. 117-121.

AUA Practice Guidelines Committee, "AUA Guideline on Management of Benign Prostatic Hyperplasia (2003), Chapter 1: Diagnosis and Treatment Recommendations," Journal of Urology, vol. 170, Aug. 2003, pp. 530-547.

Medical Advisory Secretariat. "Energy Delivery Systems for Treatment of Benign Prostatic Hyperplasia: An Evidence-Based Analysis," Ontario Health Technology Assessment Series 2006, vol. 6, No. 17, Aug. 2006, 122 pages.

(56) References Cited

OTHER PUBLICATIONS

Harkaway, R.C. and M.M. Issa. "Medical and minimally invasive therapies for the treatment of benign prostatic hyperplasia," Prostate Cancer and Prostatic Diseases, vol. 9, EPub: Jun. 6, 2006, pp. 204-214.
Hoffman, R.M. et al. "Microwave thermotherapy for benign prostatic hyperplasia (Review)," The Cochrane Library, 2009, Issue 4, pp. 1-50.
Kaye, J.D. et al. "High-Energy Transurethral Thermotherapy with CoreTherm Approaches Transurethral Prostate Resection in Outcome Efficacy: A Meta-Analysis," Journal of Endourology, vol. 22, No. 4, Apr. 2008, pp. 713-718.
English language translation of WO 2004/112902 A1, Dec. 29, 2004.
Japan Patent Office, Office Action, counterpart Japanese Patent Application 2008-551389, dated Feb. 7, 2012, 9 pages (including English translation).
PCT International Search Report, counterpart PCT/US2007/01324, dated Nov. 28, 2007, 1 page.
PCT Written Opinion, counterpart PCT/US2007/01324, dated Nov. 28, 2007, 8 pages.
Xu, et al., U.S. Appl. No. 60/817,769, filed Jun. 30, 2006.
PCT International Search Report, PCT Patent Application PCT/US2004/007563, dated Sep. 2, 2005, 1 page.
International Searching Authority, Written Opinion, PCT Patent Application PCT/US2004/007563, dated Sep. 2, 2005, 3 pages.
PCT International Preliminary Examination Report, PCT Patent Application PCT/US2004/007563, dated Mar. 20, 2006, 3 pages.
European Patent Office, Supplementary Partial European Search Report, EP Patent Application 04720378.1, dated Oct. 26, 2007, 5 pages.
European Patent Office, Examination Report, EP Patent Application 04720378.1, dated Apr. 27, 2010, 5 pages.
European Patent Office, Examination Report, EP Patent Application 04720378.1, dated Feb. 17, 2012, 4 pages.
Anichini et al., "The paradox of T cell-mediated antitumor immunity in spite of poor clinical outcome in human melanoma," Cancer Immunol Immunother, vol. 53: 855-864, 2004.
Armeanu et al., "Direct and Natural Killer Cell-Mediated Antitumor Effects of Low-Dose Bortezomib in Hepatocellular Carcinoma," Clin Cancer Res, vol. 14, No. 11: 3520-3528, 2008.
Bae et al., "Photodynamic therapy-generated tumor celllysates with CpG-ogliodeoxynucleotide enhance immunotherapy efficacy in human papillomavirus 16 (E6/E7) immortalized tumor cells," Cancer Science, vol. 98, No. 5: 747-752, 2007.
Baecher-Allan et al., "Immune regulation in tumor-bearing hosts." Current Opinion in Immunology, vol. 18: 214-219, 2006.
Benigni et al., "Phenotype and Homing of CD4 Tumor-Specific T Cells is Modulated by Tumor Bulk," The Journal of Immunology, vol. 175: 739-748, 2005.
Bromley et al., "Characterization of an antitumor immune response after light-activated drug therapy using talaporfin sodium in a spontaneously metastasizing mammary tumor model," ASCO Meeting Abstracts: 2pp, 2009.
Bunt et al., "Tumor-Associated Myeloid-Derived Suppressor Cells," Cancer Immunotherapy, Chapter 17: 309-331, 2007.
Campoli et al., "Tumor-Induced Immune Suppression and Immune Escape," Cancer Drug Discovery and Development: Immunotherapy of Cancer, Ch. 15: 263-284, 2006.
Canti et al., "Photodynamic therapy and the immune system in experimental oncology." Photochem. Photobiol. Sci. vol. 1: 79-80, 2002.
Castano et al., "Specific anti-tumor immune response with photodynamic therapy mediated by benzoporphyrin derivative and chlorine (e6)," Proceedings of SPIE, vol. 4961: 1-9, 2003.
Chen et al., "New Technology for Deep Light Distribution in Tissue for Phototherapy," Cancer J, vol. 8: 154-163, 2002.
Coukos et al., "The Tumor Microenvironment," Cancer Drug Discovery and Development: Immunotherapy of Cancer, Ch. 16: 285-301, 2006.
Danna et al., "Surgical Removal of Primary Tumor Reverses Tumor-Induced Immunosuppression Despite the Presence of Metastatic Disease," Cancer Research, vol. 64: 2205-2211, 2004.
Das et al., "Induction of apoptosis and manganese superoxide dismutase gene by photodynamic therapy in cervical carcinoma cell lines," Int J Clin. Oncol, vol. 5:97-103, 2000.
De Visser et al., "Effects of TGF-beta on the immune system: implications for cancer immunotherapy," Leukemia, vol. 13: 1188-1199, 1999.
De Visser, Karin, "Spontaneous immune responses to sporadic tumors: tumor-promoting, tumor-protective or both?" Cancer Immunol Immunother vol. 57: 1531-1539, 2008.
Derhovanessian et al., "Immunity, ageing, and cancer," Immunity & Ageing, vol. 5: 16pp, 2008.
Disis et al., "Use of tumour-responsive T cells as cancer treatment," www.thelancet.com. vol. 373: 674-683, 2009.
Emens et al., "Manipulating Immunological Checkpoints to Maximize Antitumor Immunity," Cancer Drug Discovery and Development: Immunotherapy of Cancer, Ch. 19: 331-353, 2006.
Engel et al., "A Phase II Study of Single Agent Bortezomib in Patients with Metastatic Breast Cancer: A Single Institution Experience," Cancer Inveskotion, vol. 25, No. 8: 733-737, 2007.
Finn, Olivera., "Cancer Immunology," N Engl. J Med, vol. 358, No. 25: 2704-2715, Jun. 19, 2008.
Fong et al., "Anti-Cytotoxic T-Lymphocyte Antigen-4 Antibody: The First in an Emerging Class of Immunomodulatory Antibodies for Cancer Treatment," Journal of Clinical Oncology, vol. 26, No. 32: 5275-5283, 2008.
Frumento et al., "Targeting Tumor-Related Immunosuppression for Cancer Immunotherapy," Endocrine, Metabolic, & Immune Disorders—Drug Targets, vol. 6: 223-237, 2006.
Gajewski et al., "Immune resistance orchestrated by the tumor microenvironment," Immunological Reviews, vol. 213: 131-145, 2006.
Gajewski et al., "Immune suppression in the Tumor Microenvironment," J Immunother, vol. 29, No. 3: 233-240, 2006.
Ganss et al., "Overcoming tumor-intrinsic resistance to immune effector function," Eur. J Immunol., vol. 34: 2635-2641, 2004.
Goldszmid et al., "Dendritic Cells Charged with Apoptotic Tumor Cells Induce Long-Lived Protective CD4+ and CD8+ T Cell Immunity against B16 Melonoma," The Journal of Immunology: 5940-5947, 2003.
Gollnick et al., "Generation of Effective Antitumor Vaccines Using Photodynamic Therapy," Cancer Research, vol. 62: 1604-1608, 2002.
Gollnick et al., "Photodynamic Therapy and Anti-Tumor Immunity," Lasers in Surgery and Medicine, vol. 38: 509-515, 2006.
Gollnick et al., "Photodynamic therapy (PDT) control of distant disease through immune mechanisms," Proc Amer Assoc Cancer Res, vol. 45: 2pp, 2004.
Gonzalez et al., "Effect of surgical resection of metastatic disease on immune tolerance to cancer. How a systemic disease could be controlled by a local therapy," Clin Trans' Oncol, vol. 9: 571-577, 2007.
Gravekamp et al., "Cancer vaccination: Manipulation of immune responses at old age," Mechanisms of A2e_ir,79, and Development, vol. 130: 67-75, 2009.
Gupta, Sudhir, "Molecular mechanisms of apoptosis in the cells of the immune system in human aging," Immunological Reviews vol. 205: 114-129, 2005.
Halliday et al., "Spontaneous Regression of Human Melanoma/Nonmelanoma Skin Cancer: Association with Infiltrating CD4+ T Cells," World J Surg., vol. 19: 352-358, 1995.
Hamblin et al., "Combination Immunotherapy and Photodynamic Therapy for Cancer," Proceedings of SPIE, vol. 6087: 12pp, 2006.
Hamblin et al., "Scavenger receptor-targeted photodynamic therapy of 1774 tumors in mice: tumor response and concomitant immunity," Proceedings of SPIE, vol. 4617: 1-10, 2002.
Harvey et al., "Killing tumor cells: the effect of photodynamic therapy using mono-L-aspartyl chlorine and NS-398," The American Journal of Surgery, vol. 189: 302-305, 2005.

(56) References Cited

OTHER PUBLICATIONS

Henderson et al., "Choice of Oxygen-Conserving Treatment Regimen Determines the Inflammatory Response and Outcome of Photodynamic Therapy of Tumors," Cancer Research, vol. 64: 2120-2126, 2004.
Igney et al., "Immune escape of tumors: apoptosis resistance and tumor counterattack," Journal of Leukocyte Biology, vol. 71: 907-920, Jun. 2002.
Ishikawa et al., "Perioperative immune responses in cancer patients undergoing digestive surgeries," World Journal of Surgical Oncology, vol. 7, No. 7: 22pp, 2009.
Ito, Takashi, "Cellular and Subcellular Mechanisms of Photodynamic Action: The 1O2 Hypothesis as a Driving Force in Recent Research," Photochemistry and Photobiology. vol. 28: 493-508, 1978.
Jackaman et al., "Deliberately provoking local inflammation drives tumors to become their own protective vaccine site," International Immunology, vol. 20, No. 11: 1467-1479, 2008.
Kabingu et al., "CD8+ T cell-mediated control of distant tumours following local photodynamic therapy is independent of CD4+ T cells and dependent on natural killer cells," British Journal of Cancer 1-10, 2007.
Kaufman et al., "Immune system versus tumor: shifting the balance in favor of DCs and effective immunity," The Journal of Clinical Investigation, vol. 113, No. 5: 664-667, 2004.
Kessel et al., "Mitochondrial photo damage and PDT-induced apoptosis," Journal of Photochemistry and Photobiology B, vol. 42: 89-95, 1998.
Kim et al., "Cancer Cell Immune Escape and Tumor Progression by Exploitation of Anti-Inflammatory and Pro-Inflammatory Responses," Cancer Biology and Therapy, vol. 4, No. 9: 924-933, 2005.
Kim et al., "Tumor-Driven Evolution of Immunosuppressive Networks during Malignant Progression," Cancer Res, vol. 66, No. 11: 5527-5536, 2006.
Klebanoff et al., "CD8+ T-cell memory in tumor immunology and immunotherapy," Immunol. Rev., vol. 211: 214-224, 2006.
Korbelik, M Iaden., "Advances in the understanding of host response associated with tumor PDT," BioEhotonics and Immune Responses II, Proc. of SPIE, vol. 6438: 10pp., 2007.
Korbelik et al., "Interaction Between Photodynamic Therapy and BCG Immunotherapy Responsible for the Reduced Recurrence of Treated Mouse Tumors," Photochemistry and Photobiology, vol. 73, No. 4: 403-409, 2001.
Korbelik et al., "Photodynamic therapy-generated vaccine for cancer therapy," Cancer Immunol. Immunother., vol. 55: 900-909, 2006.
Korbelik et al., "Photodynamic therapy-generated vaccines: relevance of tumour cell death expression," British Journal of Cancer 1-7, 2007.
Korbelik et al., "Photodynamic Therapy-Induced Cell Surface Expression and Release of Heat Shock Proteins: Relevance for Tumor Response," Cancer Res., vol. 65, No. 3: 1018-1026, 2005.
Korbelik et al., "Photodynamic Therapy-mediated Immune Response against Subcutaneous Mouse Tumors," Cancer Research, vol. 59: 1941-1946, 1999.
Kujundzic et al., "A Phase II Safety and Effect on Time to Tumor Progression Study of Intratumoral Light Infusion Technology Using Talaporfin Sodium in Patients With Metastatic Colorectal Cancer," Journal of Surgical Oncology: 1-7, 2007.
Lehrnbecher et al., "Changes in host defence induced by malignancies and antineoplastic treatment: implication for immunotherapeutic strategies," Lancet Oncology, vol. 9: 269-278, 2008.
Li et al., "Apoptosis and expression of cytokines triggered by pyropheophorbide—a methyl ester-mediated photodynamic therapy in nasopharyngeal carcinoma cells," Photodiagnosis and Photodynamic Therapy, vol. 3: 247-258, 2006.
Liu et al., "Overcoming Immune Tolerance to Cancer by Heat Shock Protein Vaccines," Molecular Cancer Therapeutics, vol. 1: 1147-1151, 2002.
Lustgarten, Joseph, "Cancer, aging and immunotherapy: lessons learned from animal models," Cancer Immunol. Immunother.: 11pp., 2009.
Lustig et al., "A Multicenter Phase I Safety Study of Intratumoral Photo activation, of Talaporfin Sodium in Patients with Refractory Solid Tumors," Cancer, vol. 98, No. 8: 1767-1771, 2003.
Mohebtash et al., "Phase I trial of PSA-TRICOM vaccine and ipilimumab in patients (Pts) with metastatic castrate-resistant prostrate cancer (mCRPC)," Genitourinary Cancers Symposium: Abstract only 3pp, 2009.
Molhoek et al., "Apoptosis of CD4+CD25high T cells in response to Sirolimus requires activation of T cell receptor and is modulated by IL-2," Cancer Immunol Immunother, vol. 58: 867-876, 2009.
Morton et al., "Cytoreductive Surgery and Adjuvant Immunotherapy: A New Management Paradigm for Metastatic Melanoma," CA Cancer J Clin, vol. 49, No. 2: 101-116, 1999.
Mozaffari et al., "NK-cell and T-cell functions in patients with breast cancer: effects of surgery and adjuvant chemo- and radio-therapy," British Journal of Cancer, vol. 97: 105-111, 2007.
Myrianthefs et al., "Cancer cachexia and immunomodulation," Journal of BUON, vol. 10: 181-188, 2005.
Nigam et al., "Immunomodulatory properties of antineoplastic drugs administered in conjunction with GM-CSF-secreting cancer cell vaccines," International Journal of Oncology, vol. 12: 161-170, 1998.
Nowis et al., "The influence of photodynamic therapy on the immune response," Photodiagnosis and Photodynamic Therapy, vol. 2: 283-298, 2005.
Nylandsted et al., "Selective depletion of heat shock protein 70 (Hsp70) activates a tumor-specific death program that is independent of caspases and bypasses Bcl-2," PNAS, vol. 97, No. 14: 7871-7876, 2000.
Ochsenbein, Adrian, "Principles of tumor immunosurveillance and implications for immunotherapy," Cancer Gene Therapy, vol. 9: 1043-1055, 2002.
Oseroff, Alan, "PDT as a Cytotoxic Agent and Biological Response Modifier: Implications for Cancer Prevention and Treatment in Immunosuppressed and Immunocompetent Patients," Journal of Investigative Dermatology, vol. 126: 542-544, 2006.
Pilling et al., "Prolonged Survival Due to Spontaneous Regression and Surgical Excision of Malignant Mesothelioma," The Society of Thoracic Surgeons, vol. 83: 314-315, 2007.
Pockley, A. Graham., "Heat shock proteins as regulators of the immune response," The Lancet, vol. 362: 469-476, 2003.
Preise et al., "Systemic antitumor protection by vascular-targeted photodynamic therapy involves cellular and humoral immunity," Cancer Immunol. Immunother., vol. 58: 71-84, 2009.
Prendergast, George, "Breaking Immune Suppression in Cancer: The Emerging Revolution in Immunotherapy." Cancer Reviews Online, vol. 7: 13-14, 2007.
Printz, Carrie, "Spontaneous Regression of Melanoma May Offer Insight Into Cancer Immunology," JNCI Journal of the National Cancer Institute, vol. 93, No. 14: 1047-1048, 2001.
Rabinovich et al., "Programmed Death Ligand-I and Galectin-1: Pieces in the Puzzle of Tumor-Immune Escape," Cancer Immunotherapy, Chapter 18: 333-346, 2007.
Salazar et al., "Cancer Vaccines: The Role of Tumor Burden in Tipping the Scale Towards Vaccine Efficacy," Journal of Clinical Oncology vol. 23, No. 30: 7397-7398, 2005.
Schmid et al., "A phase I/II study of bortezomib and capecitabine in patients with metastatic breast cancer previously treated with taxanes and/or anthracyclines," Annals of Oncology, vol. 19: 871-876, 2008.
Schumacher et al., "Immunosensitization of Tumor Cells to Dendritic Cell Activated Immune Responses with the Uroteasome Inhibitor Bortezomib (PS-341, Velcade)," The Journal of Immunology, vol. 176: 4757-4765, 2006.
Smyth et al., "CD4+CD25+ T Regulatory Cells Suppress NK Cell-Mediated Immunotherapy of Cancer," The Journal of Immunology, vol. 176: 1582-1587, 2006.
Spiesek et al., "Bortezomib enhances dendritic cell (DC)-mediated induction of immunity to human myeloma via exposure of cell surface heat shock protein 90 on dying tumor cells: therapeutic implications," Immunobiology, vol. 109, No. 11: 4839-4845, 2007.

(56) References Cited

OTHER PUBLICATIONS

Steal et al., "The Marriage of Growth Factor Inhibitors and Chemotherapy: Bliss or Bust?" Journal of Clinical Oncology, vol. 27, No. 10: 1545-1548, 2009.

Stewart et al., "Altered Immune Function during Long-Term Host-Tumor Interactions Can Be Modulated to Retard Autochthonous Neoplastic Growth," The Journal of Immunology: 28512859, 2007.

Stewart et al., "Immunological responses can have both pro-and antitumour effects: implications for immunotherapy," Expert Reviews in Molecular Medicine, vol. 9, Issue 4: 1-20, 2007.

Stoll, Basil A., "Spontaneous regression of cancer: new insights," Biotherapy, vol. 4: 23-30, 1992.

Tapia et al., "Activity of bortezomib, a proteasome inhibitor, in breast cancer cells: association with negative estrogen receptor and IKKINF-{kappa}B expression," ASCO Annual Meeting Abstracts: 3pp., 2005.

Thirumaran et al., "Cytotoxic Chemotherapy in Clinical Treatment of Cancer," Cancer Immunotherapy, Chapter 7: 101-116, 2007.

Thong et al., "Immune Response Against Angiosarcoma Following Lower Fluence Rate Clinical Photodynamic Therapy," Journal of Environmental Pathology, Toxicology, and Oncology, vol. 27, No. 1: 43-50, 2008.

Thong et al., "Photodynamic-therapy-activated immune response against distant untreated tumours in recurrent angiosarcoma,." Lancet Oncology, vol. 8: 950-952, 2007.

Valenti et al., "Tumor-Released Microvesicles as Vehicles of Immunosuppression," Cancer Res., vol. 67, No. 7: 2912-2915, 2007.

Van Duijnhoven et al., "The immunological consequences of photodynamic treatment of cancer, a literature review." Immunobiology, vol. 207: 105-113, 2003.

European Patent Office, European Communication, issued in European Patent Application No. 07718240.0, dated Mar. 22, 2017.

\* cited by examiner

METHOD AND APPARATUS FOR LIGHT-ACTIVATED DRUG THERAPY

CROSS-REFERENCE TO RELATED APPLICATIONS

This application is a Continuation-In-Part application of a co-pending U.S. patent application Ser. No. 15/091,270, filed on Apr. 5, 2016 which is a Continuation-In-Part application of abandoned U.S. patent application Ser. No. 12/161,323, which entered U.S. on Nov. 19, 2008 as the National Stage of International Application PCT/US2007/01324, filed Jan. 18, 2007, and published as WO 2007/084608 on Jul. 26, 2007. The International Application claims priority to Chinese Application No. 200620088987.8, filed Jan. 18, 2006. The Chinese, International, and National Stage applications are herein incorporated by reference in their entirety.

FIELD OF THE INVENTION

The present invention relates generally to a prostate treatment system for treating prostatic tissue in combination with a photoactive agent, and more specifically a transurethral device in combination with a light-activated drug for use in treating benign prostatic hyperplasia (BPH).

BACKGROUND

Benign prostatic hyperplasia (BPH) and prostate cancer are common conditions in the older male population. For people with BPH, the enlarged prostate can compress the urethra causing obstruction of the urine pathway, which results in difficulty urinating. The enlarged prostate can also cause urethral stones, inflammation, infection and in some instances, kidney failure.

Major treatment methods for BPH include surgical treatment such as a prostatectomy or transurethral resection of the prostate. These treatments require the patient to be hospitalized, which can be a financial burden to the patient. Additionally, surgical procedures can result in significant side effects such as bleeding, infection, residual urethral obstruction or stricture, retrograde ejaculation, and/or incontinence or impotence. Patients who are too old or who have weak cardiovascular functions are not good candidates for receiving these treatment methods.

Photodynamic treatment (PDT) methods are new methods for treating cancers. In light-activated drug therapy, also known as PDT, light of a specific wavelength or waveband is directed toward a target cell or cells that have been rendered photosensitive through the administration of a photoreactive, photoinitiating, or photosensitizing agent. The drug is commonly administered to the patient via intravenous injection, oral administration, or by local delivery to the treatment site. A light source emitting certain wavelength or waveband can be used to irradiate the cancerous tumor or the enlarged tissue by activating the photosensitizer to produce a strong oxidizing agent that can kill the cancerous tumor or enlarged tissues. As compared to surgical alternatives, the light-activated drug therapy is minimally invasive, less costly, and has a lower risk of complications.

One type of light delivery system used for light-activated drug therapy comprises the delivery of light from a light source, such as a laser, to the targeted cells using an optical fiber delivery system with special light-diffusing tips on the fibers. This type of light delivery system may further include optical fiber cylindrical diffusers, spherical diffusers, micro-lensing systems, an over-the-wire cylindrical diffusing multi-optical fiber catheter, and a light-diffusing optical fiber guide wire. This light delivery system generally employs a remotely located high-powered laser, or solid-state laser diode array, coupled to optical fibers for delivery of the light to the targeted cells.

The light source for the light delivery system used for light-activated drug therapy may also be light emitting diodes (LEDs) or solid-state laser diodes (LDs). LEDs or LDs may be arrayed in an elongated device to form a "light bar" for the light delivery system. The LEDs or LDs may be either wire bonded or electrically coupled utilizing a "flip chip" technique that is used in arranging other types of semiconductor chips on a conductive substrate. Various arrangements and configurations of LEDs or LDs are described in U.S. Pat. Nos. 5,445,608; 6,958,498; 6,784,460; and 6,445,011, which are incorporated herein by reference.

One of the challenges in design and production of light bars relates to size. The largest diameter of the light bar is defined by human anatomy and the smallest diameter is defined by the size of the light emitters that emit light of a desired wavelength or waveband at a sufficient energy level, and the fragility of the bar as its thickness is reduced, which increases the risk of breaking in the patient.

Presently, there exists a need for an apparatus for light-activated drug therapy for effectively treating prostate via the urethra that is cost effective, less invasive than other treatments, and has less risk of complications. Accordingly, there is a need for smaller LEDs or LDs and other light sources that are safe for use in a urethra tract introduced via a catheter-like device.

SUMMARY

The invention describes devices, methods and systems for light-activated drug therapy for treating the prostate transurethrally. One embodiment of a transurethral treatment device can include an elongated support member configured to pass through the urethra, a light delivery device, and a positioning element carried by the support member. The support member can be a catheter having at least one lumen, or in other embodiments the support member can be a generally closed body without a lumen. The light delivery device can have a light generator along the support member and a light emitting region configured to be positioned within the urethra at least proximate to a treatment site. The light generator is configured to generate light at a preselected wavelength or waveband in the range of an activation waveband of a photoactive composition. The positioning element is configured to locate the light emitting region within the urethra at least proximate to the treatment site. The positioning element, for example, can be a balloon or indicators on the support member.

In other embodiments a transurethral treatment device comprises a light delivery device positionable within or along an elongated support member for treatment of benign prostatic hyperplasia (BPH). The light delivery system may include light emitting diodes (LEDs), laser diodes (LDs), or may include a diffusion quartz fiber tip connected to an internal source of light energy. The treatment device may further include a temperature monitoring system for monitoring the temperature at the treatment site and a urine drainage system.

According to another embodiment of the invention, the treatment device has a light delivery device positioned within a catheter-like device, such as a Foley catheter or a conventional balloon catheter. In one embodiment, a light bar, sized to fit into a standard or custom optically clear Foley catheter, is inserted into the catheter which has been placed via the urethra at the prostate. The device can be used in a sterile Foley catheter or can be delivered in a sterile pack kit prepackaged with the catheter and/or an appropriate photoactive agent dose so that it is convenient for prostatic procedures, and thus facilitates treatment in a non-surgical environment leading to potential reduction in costs and medical complications.

In additional embodiments, the transurethral treatment device can have an outer diameter of about 0.8 mm to about 10 mm (e.g., 2.5 mm). The light source may have a cross-sectional dimension of about 0.5 mm to about 1.5 mm, but in other embodiments it can be larger. The size of an LED, for example, can be approximately 0.25 mm to 1 mm. In other embodiment, the transurethral treatment device, light source and LEDs can have other cross-sectional dimensions. The light bar may further include an encapsulant made from a flexible polymeric material with an appropriate refractive index to ensure efficient light coupling into the body. The encapsulant can also be made from opaque or reflective material to direct the light to the targeted tissues and to protect other tissues.

In additional embodiments, non-LED light sources such as laser diodes (LDs) can be used. Generated light can be transmitted to the treatment site via optical fibers. The light delivery system may further include a diffusion quartz fiber tip connected to a source of light.

In additional embodiments, the light emitting region of the treatment device is fixed in place in the elongated support member. In yet another embodiment, the light emitting region of the light delivery device is movable within or along the elongated support member. For example, at the end of the treatment the light delivery device may be removed and the elongated support member left in place to act as a urine drain. The treatment device may further include printed markings or indicia on the catheter to aid in placement of the light bar within the catheter.

In additional embodiments, the catheter has a selective coating to control where light transmits to the prostatic tissue thus directing the light activate drug therapy and reducing the potential to treat adjacent tissue.

According to still further embodiments, a Y-connection with a leakage control valve is included to allow the light delivery device to be inserted into the elongated support member through a separate lumen from a urine collection lumen. The elongated support member may include one or more lumens as needed to provide light transmission source manipulation and placement. In additional embodiments, the elongated support member may include a balloon to further aid in positioning the light delivery device proximate to the prostate using non-incision type methods. In additional embodiments, the catheter may include a retractable fixation device such as balloon, umbrella, tines, disk or other means for fixation and placement within the bladder.

In additional embodiments, to make the light bar visible to ultrasound, the elongated support member and light bar may include echogenic material to reflect high-frequency sound waves and thus be imageable by ultrasound techniques. Echogenic material will aid in proper placement of the elongated support member and the light bar in operation. In additional embodiments, the light delivery system also includes temperature sensors which are electrically connected to temperature monitors for monitoring temperature at the treatment site.

Several embodiments of the present invention are expected to provide efficient, low cost, and minimally-invasive treatments of prostate conditions. The treatment device may be used to treat prostate cancer, prostatits, cystitis, bladder cancer, hypertrophic trigone, and hypertrophic urethral sphincter. The present invention utilizes light-activated drug therapy to minimally-invasively treat BPH or prostate cancer via the urethra. As a result, patients with BPH or prostate cancer can be treated using the present invention without being admitted to a hospital, undergo general anesthesia and blood transfusion, and thus have lower risk of complications.

For many of the described embodiments, a photosensitizer is administered intravenously before activating the light delivery device. The light activates the photosensitizer to promote cell death in the prostatic tissue. The device provides a minimally invasive transurethral method for treating BPH, prostate cancer or other prostatic conditions. This type of light-activated drug therapy would treat prostatic tissue, for example, by causing cell death in the prostatic tissue. Such cell death and the absorption of the tissue by the patient's body would create an opening for urine to flow from the bladder out the urethra.

The invention also provides methods of administering light-activated drug therapy to treat targeted tissue of a human or non-human patient. In one embodiment, the method includes identifying a location of tissue to be treated in the prostate; inserting an elongated support member into the urethral tract to position a light emitting region at least proximate to the location of the targeted tissue; and administering an effective dose of a photoactive composition to the targeted tissue. The method may include confirming placement of the light source prior to treatment. The method further includes treating the targeted tissue with light-activated drug therapy for a predetermined period of treatment.

In some embodiments, the light-activated drug is mono-L-aspartyl chlorine $e_6$, also referred to herein as Talaporfin Sodium. This compound's absorption spectrum has several absorption bands: 400-420 nm (e.g., peak of about 411 nm), 500-520 nm (e.g., peak of about 507 nm), and 655-670 nm (e.g., peak of about 664 nm). The drug could be excited at any of these bands. Alternative light-activated drugs of suitable excitation wavelengths may also be used as is known in the art.

BRIEF DESCRIPTION OF THE DRAWINGS

The following drawings are intended as an aid to an understanding of the invention to present examples of the invention, but do not limit the scope of the invention as described and claimed herein. In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with light sources, catheters and/or treatment devices have not been shown or described in detail to avoid unnecessarily obscuring descriptions of the embodiments of the invention.

Generally, a prostate treatment system can include a transurethral treatment device having a light delivery device positioned within or along an elongated support member for treatment of benign prostate hyperplasia (BPH) and other prostate conditions. In one embodiment, the treatment device includes a light delivery device disposed on the surface of the elongated support member, or in other embodiments, the light delivery device is within a lumen of the elongated support member. The light generator can be optically connected to a light emitting region via optical fibers or light guides. Alternatively, the light generator and the light emitting region may be positioned together at the distal end of the elongated member at least proximate to a treatment site. Thus, the light generator may include a laser, an LED, a thin plastic sheet material which produces light at a selected wavelength or waveband, or other suitable light sources that can be transmitted to or placed at the treatment site. According to a further embodiment of the invention, the transurethral treatment device also includes temperature sensors which are electrically connected to temperature monitors.

A. Treatment Device for Treating Benign Prostate Hyperplasia (BPH)

Figure 1:
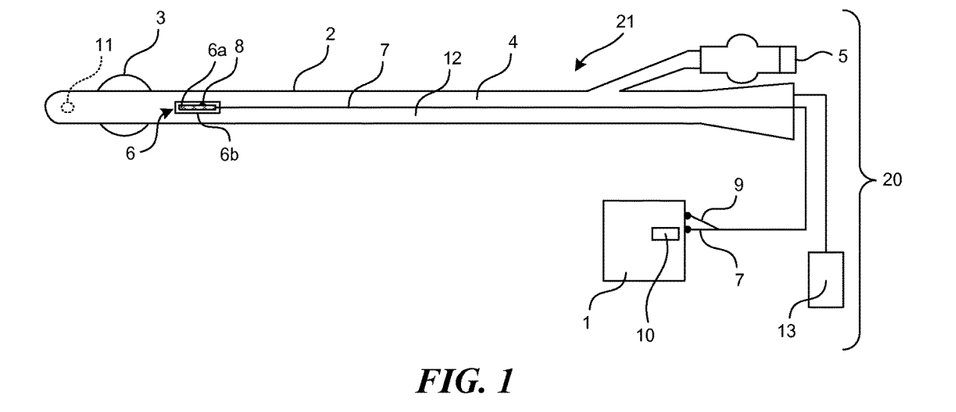
FIG. 1 is an elevational side view of a prostate treatment system having a transurethral treatment device according to one embodiment of the invention.

FIG. 1 illustrates a prostate treatment system 20 including a power supply 1 and a transurethral treatment device 21 having an elongated support member 2 and a light delivery device 6 positioned along or within the support member 2. The transurethral treatment device 20 may further includes a balloon 3 or other type of positioning element carried by the elongated support member 2. The support member 2 can be a catheter having a lumen 4, or the support member 2 can be a closed body without a lumen. According to an embodiment, the support member 2 has a total length of 400 to 450 mm and has an outer diameter of 3.327 mm, and the balloon 3 at the distal end of the support member 2 has a volume of 10 to 30 ml and is used to position and fix the light delivery device 6 proximate to the treatment site such as the prostate.

The light delivery device 6 can have a light generator 6a and a light emitting region 6b. In the embodiment shown in FIG. 1, the light generator 6a and the light emitting region 6b are at approximately the same location of the elongated member, but in other embodiments shown below, the light generator 6a may not be coincident with the light emitting region 6b. As shown below, the light generator 6a may be located towards the proximal end of the support member 2. When the support member 2 is a catheter with a lumen 4, the light delivery device 6 can move within the lumen to be positioned relative to the treatment site. In other embodiments, the light delivery device 6 can be disposed on the surface of the catheter 2 below the balloon 3 or other type of positioning element. The power for the light generator can be transmitted to the light delivery device 6 via a lead wire 7 coupled to the power source 1. According to an embodiment of the invention, light could be emitted by a light emitting diode (LED), a laser diode, light-emitting polymer, or a quartz fiber tip optically coupled to another internal source of light energy.

Figure 2:
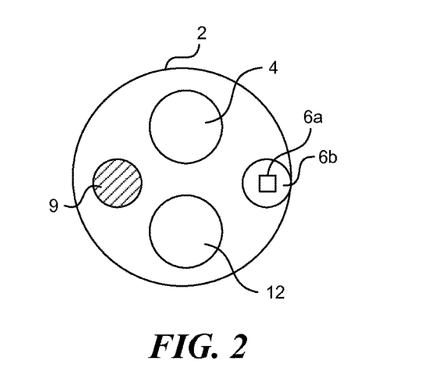
FIG. 2 is a cross-sectional view taken along line 2-2 of FIG. 1 illustrating one embodiment of lumens in the transurethral treatment device.

As illustrated in FIG. 2, the support member 2 can include a plurality of lumens therein. For example, the balloon 3 is connected to a fluid inlet 5 via lumen 4. Gas or liquid can be pumped into inlet 5 and through lumen 4 to inflate balloon 3. Referring to FIGS. 1 and 2 together, the transurethral treatment device 21 can optionally have a urine aperture 11 positioned at the distal end of the support member 2 that is connected to a urine collection bag 13 via a urine lumen 12. The urine aperture 11 can be used to collect the patient's urine during treatment.

The transurethral treatment device 21 can also optionally include a temperature measuring system having at least one of a temperature sensor 8 and a temperature monitor 10. The temperature sensor 8 can be a thermocouple or other sensor as is known in the art. The temperature sensor 8 is disposed on or thermally coupled to a surface of the support member 2 and is electrically connected to the temperature monitor 10 via wires 9 disposed within the support member 2. The temperature sensor 8 measures a temperature at the treatment site, for example, proximate to the prostate during treatment. A control loop (not shown) may further be connected to the temperature monitor 10 to automatically shut the treatment device off in the event that the temperature at the treatment site exceeds a predetermined value. Alternatively, the temperature monitor 10 may further include a warning device (not shown), such as a visual indicator or audible indicator, to provide an operator with a warning that a predetermined temperature has been reached or is being exceeded during treatment.

Figure 3:
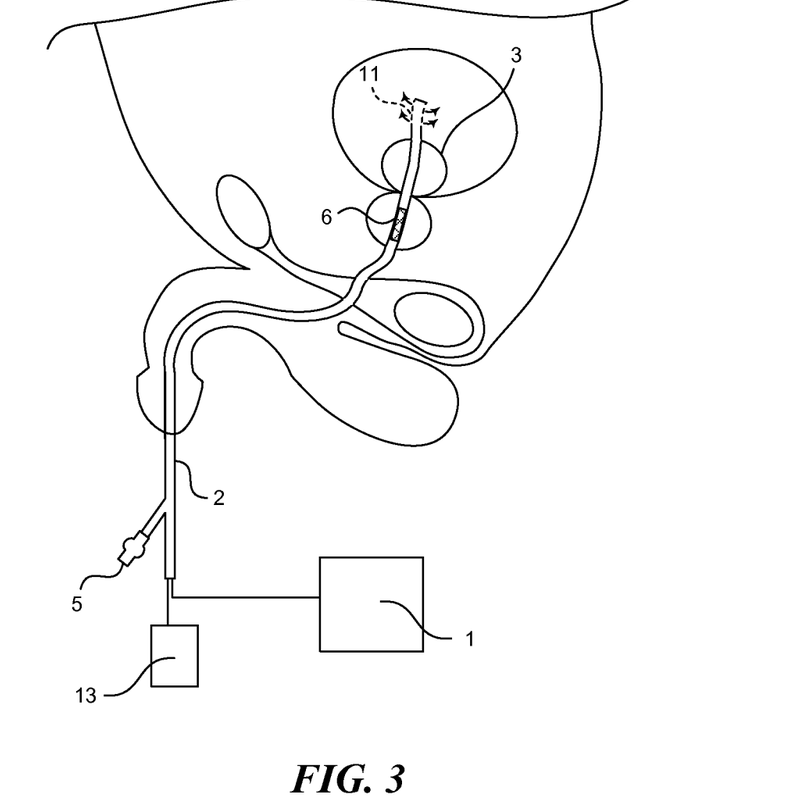
FIG. 3 is side view of a transurethral treatment device positioned in the urethra tract of a patient according to an embodiment of the invention.

As illustrated in FIG. 3, the treatment device is positioned transurethrally to allow access to the prostate, followed by administration of a photoactive drug, by injection, intravenously, or orally. The transurethral treatment device 21, and more specifically a portion of the support member 2, can be directed into the urethra under topical anesthesia. Once the support member is positioned, 4 to 10 ml of saline or air can be pumped into the balloon 3 via the air pumping channel 4 to inflate the balloon 3. After inflation of the balloon 3, the support member 2 can be pulled slightly proximally such that the balloon 3 can be fixed at the inner opening of the urethra. Accordingly, the light delivery device 6 can be positioned at least proximate to or within the prostate. The photoactive drug can then be administered to the patient, and the light generator 6b can be activated.

The support member 2 has a proximal portion and a distal portion relative to a power controller. The distal portion of support member 2 includes the light delivery device 6. In one embodiment, the light delivery device comprises a plurality of LEDs in electrical communication with the power supply via lead wires 7 as shown in FIG. 1. The lead wires may be selected from any suitable conductor that can be accommodated within the dimensions of the support member, for example: a bus bar that electronically couples the LEDs to the controller; flexible wires; a conductive film or ink applied to a substrate, and the like. Additionally or alternatively, the light delivery device may include Bragg reflectors to better control the wavelength of the light that is to be transmitted to the target cells.

A power controller 1 may be programmed to activate and deactivate LEDs of a light delivery device in a pulsed sequence or a continuous sequence. For example, the LEDs may form two halves of the light array that may be turned on and off independently from each other. Alternatively, the system may be programmed to selectively activate and deactivate (e.g., address) different selected individual or groups of LEDs along the length of the bar. In this manner, a treatment protocol, for example causing the LEDs to be lit in a certain sequence or at a particular power level for a selected period of time, may be programmed into the controller. Therefore, by selectively timing the pulses and/or location of the light, the system delivers light in accordance with a selected program. Alternatively, LEDs can be powered by DC continuously. Examples of addressable light transmission arrays are disclosed in U.S. Pat. No. 6,096,066, herein incorporated in its entirety by reference. Exemplary light transmission arrays which include shielding or distal protection are disclosed in U.S. patent application Ser. Nos. 10/799,357 and 10/888,572, herein incorporated in their entirety by reference.

Without being bound by any theory, applicants believe that by delivering light in pulses, the efficacy of the light-activated drug therapy is improved, given that the treated tissue is allowed to reoxygenate during the cycles when the light is off. Applicants further believe that tissue oxygenation during therapy is improved by using a lower frequency. In one embodiment the operational frequency is 50 Hz-5 kHz, and in one embodiment, is 50-70 Hz.

According to a further embodiment of the invention, the treatment device may further include a temperature monitoring system for monitoring the temperature at the treatment site.

In one embodiment, the support member 2 is a Foley catheter and the light delivery device 6 is disposed in the Foley catheter. Alternatively, the treatment device has a light delivery device disposed in a conventional balloon catheter. Foley catheters are available in several sub-types, for example, a Coude catheter has a 45° bend at the tip to allow easier passage through an enlarged prostate. Council tip catheters have a small hole at the tip which allows them to be passed over a wire. Three-way catheters are used primarily after bladder, prostate cancer or prostate surgery to allow an irrigant to pass to the tip of the catheter through a small separate channel into the bladder. This serves to wash away blood and small clots through the primary arm that drains into a collection device.

Figure 4:
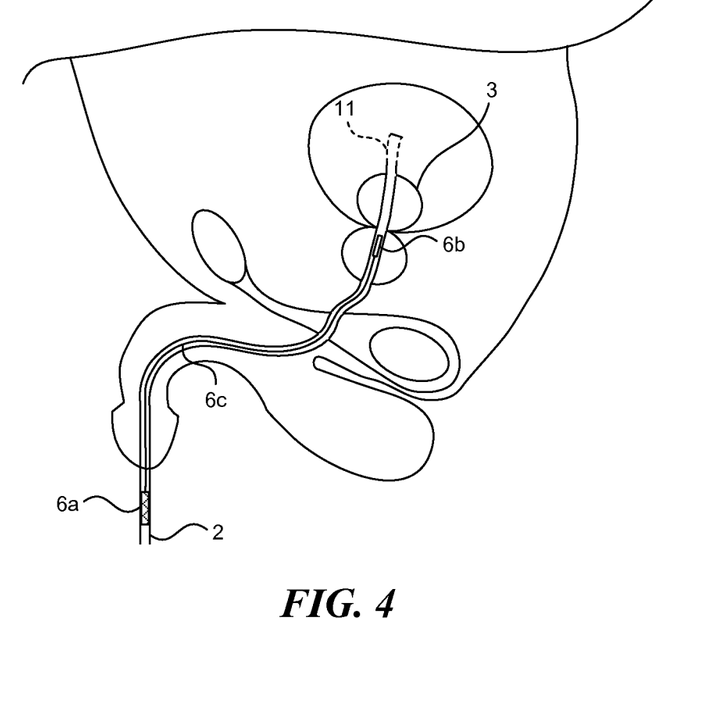
FIG. 4 is a cross-sectional view of a transurethral treatment device in accordance with another embodiment of the invention.

FIG. 4 is a cross-sectional view of still another embodiment of a transurethral treatment device 21. In this embodiment, the light delivery device includes a light generator 6a along the support member 2 at a location that is either within or external (shown) to the patient. The light delivery device can further include a light emitting region 6b positioned at least proximate to the treatment site and a light transmitting region 6c (e.g., fiber optic) between the light generator 6a and the light emitting region 6b. In FIG. 4, the support member 2 can be a catheter through which the light delivery device 6 can be moved for positioning, or the support member can be a closed body to which the light delivery device 6 is attached (e.g., fixed at a set position).

Figure 5:
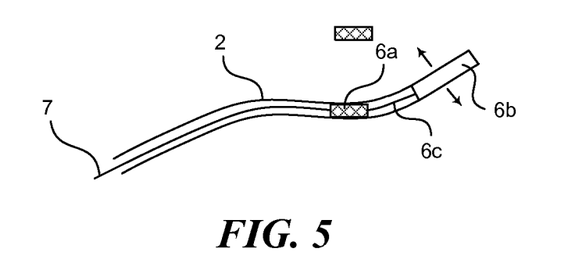
FIG. 5 is a cross-sectional view of a transurethral treatment device in accordance with yet another embodiment of the invention.
Figure 6:
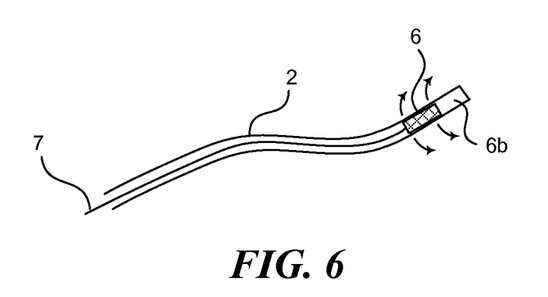
FIG. 6 is a cross-sectional view of a transurethral treatment device in accordance with still another embodiment of the invention.
Figure 7:
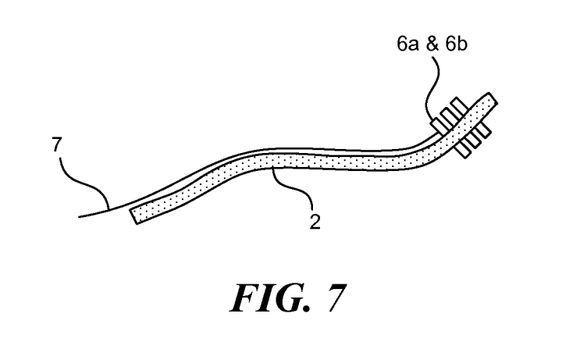
FIG. 7 is a cross-sectional view of a transurethral treatment device in accordance with another embodiment of the invention.

FIGS. 5-7 are cross-sectional views showing additional embodiments of portions of transurethral treatment devices. FIG. 5, more specifically, shows a device having a closed body support member 2 and a light delivery device fixed to the support member 2. The light delivery device has a light generator 6a, a light emitting region spaced apart from the light generator 6a distally along the support member 2, and a light transmitting region 6c between the light generator 6a and the light emitting region 6b. The light transmitting region 6c conducts light from the light generator 6a to the light emitting region 6b. FIG. 6 illustrates a device having a solid or otherwise lumen-less support member 2 and a light delivery device 6 with a light generator 6a and a light emitting region 6b at the same location longitudinally along the support member 2. In FIGS. 5 and 6, the light generator is within the support member 2. FIG. 7 shows still another embodiment in which the light delivery device is on a surface of the support member. More specifically, the light delivery device 6 has the light generator 6a and the light emitting region 6b disposed on an external surface of the support member.

In one embodiment, a light delivery system that is sized to fit into a standard or custom optically clear Foley catheter is inserted into that catheter which has been placed via the urethra at the prostate. The light delivery device can be used with a sterile Foley catheter or can be delivered in a sterile pack kit prepackaged with the catheter and/or an appropriate photoactive agent dose so that it is convenient for prostatic procedures.

The light bar or light array may include a plurality of LEDs contained in a catheter assembly or otherwise attached to a closed elongated support member. The support member 2 may have an outer diameter of about 0.8 to about 10 mm. Example of LED arrays are disclosed in U.S. application Ser. No. 11/416,783 entitled "Light Transmission system for Photo-reactive Therapy," and U.S. application Ser. No. 11/323,319 entitled "Medical Apparatus Employing Flexible Light Structures and Methods for Manufacturing Same," herein incorporated in their entirety by reference.

Additional embodiments have a power controller drive circuit capable of producing constant current D.C., A.C., square wave and pulsed wave drive signals. This is accomplished by combining a constant source with a programmable current steering network allowing the controller to selectively change the drive wave form. For example, the steering network may be modulated to achieve the various functions described above, for example, producing the desired impedance to fully discharge the battery. Furthermore, use of an A.C. drive allows for a two-wire connection to the LEDs, thereby reducing the cross-sectional diameter of the catheter, while still permitting use of two back-to-back emission sources, that when combined, produce a cylindrical light source emission pattern.

Therefore, as discussed above, the transurethral treatment device 21 can comprise a unitary, single use disposable system for light-activated drug therapy. It should be noted that in certain embodiments the catheter is fused to the power controller to form an integrated single unit. Any attempt to disconnect the support member in this embodiment results in damage to either the catheter, or module, or both.

The prostate treatment system can be used in connection with any light-activated drug of which there are many known in the art and some of which are listed in U.S. Pat. No. 7,015,240 which is fully incorporated by reference with regard to disclosed photoactive compositions. In one particular embodiment, the light-activated drug is Talaporfin Sodium. Talaporfin Sodium is a chemically synthesized photosensitizer, having an absorption spectrum that exhibits a maximum peak at 664 nm. In one embodiment, the Talaporfin Sodium is presented as a lyophilized powder for reconstitution. One hundred milligrams of Talaporfin Sodium is reconstituted with 4 milliliters of 0.9% isotonic sterile sodium chloride solution, to give a solution at a concentration of 25 mg/ml.

The drug must be activated with light, and light energy is measured here in Joules (J) per centimeter of length of the light transmitting array. Likewise the fluence of light is measured in milli-watts (mW) per centimeter of length of the light emitting array. Clearly, the amount of energy delivered will depend on several factors, among them: the photoactive agent used, the dose administered, the type of tissue being treated, the proximity of the light array to the tissue being treated, among others. The energy (E) delivered is the product of the fluence (F) and the time period (T) over which the fluence is delivered: $E = F \times T$. The fluence may be delivered for only a fraction of the treatment time, because the light array may be pulsed, for example in a frequency such as 60 kHz, or may be controlled by a timing pattern. An example of a timing pattern is that the array is at full fluence for 20 seconds, then off for 10 seconds in a repetitive cycle. Of course, any pattern and cycle that is expected to be useful in a particular procedure may be used. The control module may further be programmable in embodiments for such fractionated light delivery.

In accordance with an embodiment, fifteen minutes to one hour following Talaporfin Sodium administration, light energy in the range from about 50 to about 1000 $J/cm^2$ of light array fluence in the range from about 5 to about 50 $mW/cm^2$ of light array is delivered to the treatment site. As may be expected, the equation discussed above relating energy time and fluence plays a role in selection of the fluence and energy delivered. For example, depending upon the patient, a certain time period may be selected as suitable. In addition, the nature of treatment might dictate the energy required. Thus, fluence F is then determined by $F = E/T$. The light array should be capable of providing that fluence in the allotted time period. For example, if a total of 200 $J/cm^2$ of light array must be delivered to the treatment site at 20 $mW/cm^2$ of light array, then the treatment period is approximately 2.8 hours.

In additional embodiments, the support member further has a selective coating to control where light transmits to the prostatic tissue thus directing the light activate drug therapy and reducing the potential to treat adjacent tissue.

In another embodiment, the light delivery device is fixed in place in the catheter. In yet another embodiment, the light delivery device is movable within the catheter. According to this embodiment, the treatment device may further include printed markings or indicia on the catheter to aid in placement of the light bar within the catheter. The light delivery device can also have asymmetric light delivery to protect the colon or rectum. For example, the light deliver device can be double sided and/or shielded so that one side of the light bar emits light at a higher intensity than another side. Exemplary light delivery devices are disclosed in U.S. Pat. No. 5,876,427, herein incorporated in its entirety by reference.

In additional embodiments, a Y-connection with a leakage control valve is included to allow the light transmission source to be inserted into the catheter through a separate lumen from a urine collection lumen. The catheter may include two or more lumens as needed to provide light transmission source manipulation and placement.

In additional embodiments, the catheter includes a balloon or other positional element to further aid in positioning the light source transmission end proximate to the prostate using non-incision type methods. In additional embodiments, the catheter may include a retractable fixation device such as balloon, umbrella, tines, disk or other means for fixation and placement within the bladder.

In additional embodiments, to make the light bar visible to ultrasound, the light source catheter and/or the light bar may include echogenic material to reflect high-frequency sound waves and thus be imageable by ultrasound techniques. In operation, echogenic material will aid in proper placement of the catheter and the light source.

In additional embodiments, the light transmission source also includes temperature sensors which are electrically connected to temperature monitors.

Several embodiments of the prostate treatment systems are expected to provide highly efficient, low cost, and minimally-invasive treatment of prostate conditions. The treatment device may be used to treat prostate cancer, prostatis, cystitis, bladder cancer, hypertrophic trigone, and hypertrophic urethral sphincter. The present invention utilizes light-activated drug therapy methods to minimally-invasively treat BPH or prostate cancer via the urethra. As a result patients with BPH or prostate cancer can be treated using the present invention without being hospitalized, undergo general anesthesia and blood transfusion, and thus have lower risk of complications.

B. Methods of Treating BPH Using the Treatment Device

The invention also provides methods of administering photoactive therapy to treat targeted tissue of a human or non-human patient. In one embodiment, the method includes identifying a location of tissue to be treated in the prostate; inserting a catheter into the urethra tract; inserting a light delivery device at least proximate to the location of the targeted tissue; and administering an effective dose of a photoactive drug. The method may include confirming placement of the light source prior to treatment. The method further includes treating the targeted tissue by activating the light delivery device for a predetermined period of treatment. In some embodiments, the light-activated drug is mono-L-aspartyl chlorine $e_6$, also referred to herein as Talaporfin Sodium. Compositions and methods of making Talaporfin Sodium are disclosed and taught in U.S. provisional patent application Ser. No. 60/817,769 entitled "Compositions and Methods of Making a Photoactive Agent" filed Jun. 30, 2006, and priority to U.S. Pat. No. 8,198,312, both herein incorporated in their entirety. This compound has an absorption spectrum that exhibits several peaks, including one with the excitation wavelength of 664 nm, which is the wavelength favored when it is used in photoreactive therapy. Alternative light-activated drugs of suitable excitation wavelengths may also be used as is known in the art.

The method further includes monitoring a temperature at treatment site. The temperature measuring system includes a temperature sensor for monitoring the temperature at the treatment site. The temperature sensor may be a thermal couple or any suitable device for providing temperature information at the treatment site. The temperature sensor may be disposed at the surface of the support member and is further electrically connected to the temperature monitor via wires. Alternatively, the temperature sensor may be wirelessly connected to the temperature monitor. The temperature sensor provides the temperature proximate to the treatment site during treatment to ensure safe operating temperatures during the treatment at the treatment site.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to light sources, catheters and/or treatment devices, not necessarily the exemplary light sources, catheters and/or treatment devices generally described above.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the claimed invention.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Embodiments of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all catheters, light transmission sources and treatment devices that operate in accordance with the claims. Accordingly, the invention is not limited by the disclosure, but instead its scope is to be determined entirely by the following claims.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A transurethral light activated drug therapy device for the treatment of prostate conditions comprising:
    an elongated support member configured to pass through the urethra, the elongated support member having a proximal end and a distal end;
    a light delivery device having a light generator along the elongated support member and a light emitting region configured to be positioned within the urethra at least proximate to a treatment site, wherein the light generator is configured to generate light at a preselected wavelength or waveband in the range of an activation waveband of a photoactive composition; and
    a positioning element carried by the elongated support member, wherein the positioning element is configured to locate the elongated support member within the urethra; and
    wherein the elongated support member is a catheter having:
        a first lumen for delivering fluid to the positioning element;
        a second lumen for accommodating the light delivery device; and
        a selective coating to control where light transmits to the prostatic tissue.

2. The transurethral light-activated drug therapy device of claim 1, wherein the light generator comprises at least one or more of a light emitting diode (LED), solid-state laser diode (LD), a light-emitting polymer, a laser, a light-emitting transistor, or another light source transmitting fiber through which light can be conducted.

3. The transurethral light-activated drug therapy device of claim 1 wherein the light generator comprises an array of LEDs having a size from 0.25 mm to 1 mm.

4. The transurethral light-activated drug therapy device of claim 3 wherein the array of LEDs is configured to provide 50 J/cm$^2$ to 1000 J/cm$^2$ of light fluence.

5. The transurethral light-activated drug therapy device of claim 4 wherein the array of LEDs is configured to provide 200 J/cm$^2$ of light fluence.

6. The transurethral light-activated drug therapy device of claim 3, further comprising a power controller configured to pulse the array according to a frequency or according to a timed pattern.

7. The transurethral light-activated drug therapy device of claim 3 wherein the array of LEDs has an operational frequency in the range from 50 Hz to 5 kHz.

8. The transurethral light-activated drug therapy system of claim 2, wherein the light generator comprises an array of LEDs and the array can move axially within the catheter.

9. The transurethral light-activated drug therapy system of claim 2, wherein the light generator comprises an array of LEDs and the array is fixed at a selected location within the catheter during treatment.

10. The transurethral light-activated drug therapy device of claim 1 wherein the light delivery device is fixed to the support member.

11. The transurethral light-activated drug therapy device of claim 1 wherein the positioning element includes a balloon at the distal end of the catheter.

12. The transurethral light-activated drug therapy system of claim 1 wherein the positioning element is a balloon, umbrella, tines, and/or disk.

13. The transurethral light-activated drug therapy system of claim 1 wherein the positioning element is retractable.

14. The transurethral light-activated drug therapy system of claim 1, further comprising echogenic markings on the distal end of the catheter or on the light source or both.

15. The transurethral light-activated drug therapy system of claim 1, further comprising positioning indicia on the proximal end of the catheter.

16. A transurethral light-activate drug therapy system for the treatment of prostate conditions in a male animal having an enlarged prostate, comprising:
    a photoreactive agent comprising mono-L-aspartyl chlorine e6; and a transurethral light activate drug therapy device comprising:
- a flexible elongated support member configured to pass through a urethra of the male animal, the flexible elongated support member having a proximal end and a distal end;
- a light delivery device having a light generator carried by a distal region of the flexible elongated support member, the light generator and a light emitting region are configured to be positioned within the urethra to deliver light to the prostate, wherein the light generator is configured to generate a light band with a peak at a preselected wavelength of 664 nm radially at 360 degrees;
- a power source external to the flexible elongated support member, in flexible electrical communication with the light generator; and
- a positioning element carried by the flexible elongated support member, wherein:
- the positioning element is configured to locate the flexible elongated support member within the urethra;
- a majority of the portion of the flexible elongated support member inserted into the urethra of the male animal does not permit light from the light generator to pass through;
- a transparent or translucent, integral window along a portion of the length of the flexible elongated support member that is proximate to the prostate when the distal end of the support member is positioned in the bladder of the male animal and allows light from the light generator to pass through the window, and the window extends 360 degrees radially from the flexible elongated support member;
- the length of the light generator is at least as long as a majority of the length of the window;
- a majority of the length of the light generator is fixed in place within the window;
- when the flexible elongated support member is completely removed from the urethra, the light generator is completely removed from the urethra; and
- the flexible elongated support member is a catheter and comprises a selective coating to form the window to control where light transmits to the prostatic tissue;
- a first longitudinal internal lumen through a majority length of the flexible elongated support member for delivering fluid to the positioning element; and
- a second longitudinal internal lumen through the majority length of the flexible elongated support member for accommodating the light delivery device.

17. The transurethral light-activated drug therapy device of claim 1, wherein the elongated support member includes a third lumen, the third lumen being a urine lumen in connection to a urine collection bag.

18. The transurethral light-activated drug therapy device of claim 1, wherein the elongated support member includes a fourth lumen for accommodating a wire that connects a temperature sensor that measure a temperature at the treatment site to a temperature monitor.

19. The transurethral light-activate drug therapy system of claim 16, wherein the transurethral light activate drug therapy device includes a third lumen, the third lumen being a urine lumen in connection to a urine collection bag.

20. The transurethral light-activate drug therapy system of claim 16, wherein the transurethral light activate drug therapy device includes a fourth lumen for accommodating a wire that connects a temperature sensor that measure a temperature at prostate to a temperature monitor.

\* \* \* \* \*